United States Patent [19]
Gilbert et al.

[11] Patent Number: 5,711,944
[45] Date of Patent: Jan. 27, 1998

[54] INTERFERON POLYMER CONJUGATES

[75] Inventors: Carl W. Gilbert, Basking Ridge; Myung-Ok Cho, Highland Park, both of N.J.

[73] Assignee: Enzon, Inc., Piscataway, N.J.

[21] Appl. No.: 337,567

[22] Filed: Nov. 10, 1994

Related U.S. Application Data

[63] Continuation-in-part of Ser. No. 150,643, Nov. 10, 1993, abandoned.

[51] Int. Cl.⁶ .................................................. A61K 38/21
[52] U.S. Cl. ...................................... 424/85.7; 530/402
[58] Field of Search ............................ 424/85.7; 530/402

[56] References Cited

U.S. PATENT DOCUMENTS

| | | | |
|---|---|---|---|
| 4,179,337 | 12/1979 | Davis et al. | 435/181 |
| 4,275,000 | 6/1981 | Ross | 260/112 R |
| 4,609,546 | 9/1986 | Hiratani | 424/83 |
| 4,680,338 | 7/1987 | Sundoro | 525/54.1 |
| 4,766,106 | 8/1988 | Katre et al. | 514/12 |
| 4,894,226 | 1/1990 | Aldwin et al. | 424/85.2 |
| 4,904,582 | 2/1990 | Tullis | 435/6 |
| 4,917,888 | 4/1990 | Katre et al. | 424/85.91 |
| 4,935,465 | 6/1990 | Garman | 525/54.1 |
| 5,004,605 | 4/1991 | Hershenson et al. | 424/85.6 |
| 5,109,120 | 4/1992 | Ueno et al. | 530/351 |
| 5,122,614 | 6/1992 | Zalipsky | 548/520 |
| 5,281,698 | 1/1994 | Nitecki | 530/351 |
| 5,283,317 | 2/1994 | Saifer et al. | 528/405 |
| 5,382,657 | 1/1995 | Karasiewicz et al. | 530/351 |
| 5,559,213 | 9/1996 | Hakimi et al. | 530/351 |

FOREIGN PATENT DOCUMENTS

| | | |
|---|---|---|
| 0154316 | 9/1985 | European Pat. Off. |
| 0236987 | 9/1987 | European Pat. Off. |
| 0510356 | 10/1992 | European Pat. Off. |
| 0584876 | 3/1994 | European Pat. Off. |
| WO9101758 | 2/1991 | WIPO |
| WO9216555 | 10/1992 | WIPO |

OTHER PUBLICATIONS

Zalipsky, et al., Attachment of Drugs to Polyethlene Glycols, Eur. Ploym. J., vol. 19, No. 12, pp. 1177-1183 (1983).

*Primary Examiner*—Chhaya D. Sayala
*Attorney, Agent, or Firm*—Roberts & Mercanti, LLP

[57] ABSTRACT

A process is disclosed for preparing long-acting alpha interferon-containing compositions. Alpha interferon is contacted with a relatively small molar excess of a substantially non-antigenic polymer in the presence of a surfactant to preserve bioactivity. Isolation of the desired conjugate species having optimal activity is also disclosed.

28 Claims, No Drawings

INTERFERON POLYMER CONJUGATES

This application is a continuation-in-part of U.S. patent application Ser. No. 08/150,643 filed Nov. 10, 1993, now abandoned.

BACKGROUND OF THE INVENTION

The present invention is directed to long-acting interferon-containing preparations.

Conjugating biologically-active proteins to polymers has been suggested to improve one or more of the properties of circulating life, water solubility or antigenicity in vivo. For example, some of the initial concepts of coupling peptides or polypeptides to polyethylene glycol (PEG) and similar water-soluble polymers are disclosed in U.S. Pat. No. 4,179,337, the disclosure of which is incorporated herein by reference.

Insulin and hemoglobin were among the first therapeutic agents conjugated. These relatively large polypeptides contain several free $\epsilon$-amino attachment sites. Several polymers could be attached without significant loss of biologic activity.

The conjugation process, however, is not without complications. Excessive polymer conjugation or reactions using molar excesses of polymers beyond certain ratios have resulted in inactive conjugates. Problems often result when a therapeutic moiety's active site (i.e. where groups associated with bioactivity are found) becomes blocked by polymer attachment. This problem can be difficult to avoid since the polymer and protein are typically joined in solution-based reactions. Pre-blocking the active sites with materials such as pyridoxal phosphate have been suggested, but the results have been inconsistent. The problems are particularly acute with lower molecular weight proteins and peptides. These bioactive materials often have few attachment sites not associated with bioactivity.

Interferons are a particular example of proteins which could benefit from improved polymer conjugation techniques. See, for example, U.S. Pat. Nos. 4,766,106 and 4,917,888 which describe inter alia beta interferon conjugated with methoxypolyethylene glycol N-succinimidyl glutarate or methoxypolyethylene glycol N-succinimidyl succinate. The conjugation reactions were carried out using relatively high molar excesses (10, 20 and 50-fold) of the polymer.

European Patent Application bearing publication No. 0 236 987 describes reacting alpha and gamma interferons with high molar excesses of alkyl imido ester-activated polyethylene glycols. European Patent Application bearing publication No. 0 510 356 describes conjugating alpha interferon with pyridinyl carbonyl and thiocarbonyl activated PEG. In both cases, the reactions were not carried out in the presence of surfactants nor were the conjugated species fractionated to isolate the most desired conjugate species.

In spite of the above-described disclosures, the interferon-polymer conjugates have been unacceptable. One of the chief drawbacks has been that the level of retained interferon activity has been too low. Further, some conjugation reactions have been too low-yielding to be economical.

The present invention addresses these shortcomings.

SUMMARY OF THE INVENTION

One aspect of the invention provides a process for preparing long-acting alpha-interferon-containing compositions. The process includes contacting alpha-interferon with a substantially non-antigenic polymer in the presence of a surfactant under conditions which are sufficient to effect conjugation of the protein and polymer. Suitable alpha-interferons include recombinant and alpha-interferons isolated from mammals.

The polymer portion of the conjugate is preferably a polyalkylene oxide (PAO), such as mono-alkyl terminated PAO's like mono-methyl polyethylene glycol (mPEG). The non-alkyl-terminated end of the polymer is functionalized with a reactive group capable of bonding with the alpha-interferon, preferably at the epsilon ($\epsilon$) amino acid lysines. The polymers may have a molecular weight of from about 200 to about 35,000. Other substantially non-antigenic polymers can also be used.

The conditions for effecting conjugation include conducting the reaction with a relatively small molar excess of the polymer with respect to the alpha-interferon. The range of molar excess for the polymer can be from about 1 to 8-fold; molar excesses of from about 1.5 to 7 are preferred and a range of from about 1.75–5-fold are particularly preferred.

The conditions further include contacting the reactants in the presence of a surfactant which is present in amounts ranging from about 0.1 to about 1% by weight. One particularly preferred ionic surfactant is sodium dodecyl sulfate (SDS). Other ionic and non-ionic surfactants can also be used.

The resulting conjugates can have from about 0 to about 6 polymeric strands attached to each alpha-interferon molecule. After conjugation, those species containing about 1–4 polymer strands per IFN and most preferably those conjugates containing about 2 polymer strands per IFN molecule are fractionated away from the other species.

The invention also includes methods of treating alpha-interferon susceptible conditions in mammals. In this aspect, treatment includes administering an effective amount of the conjugates described herein to mammals requiring such therapy.

As a result of the present invention, highly active, long lasting alpha-interferon-containing conjugates are provided. In preferred embodiments, the isolated species provide predictable, uniform activity.

For a better understanding of the present invention, reference is made to the following description.

DETAILED DESCRIPTION OF THE INVENTION

1. Interferons

The alpha-interferon ($\alpha$-IFN) portion of the polymer conjugate can be prepared or obtained from a variety of sources including recombinant techniques such as those using synthetic genes expressed in *E. coli*. See also Pestka, "Interferon $\alpha$" in *Human Cytokines*, Blackwell Scientific Publications 1–16 (1992), the disclosure of which is incorporated herein by reference. In addition, the $\alpha$IFN can also be a mammalian extract such as human, ruminant or bovine $\alpha$INF. One particularly preferred $\alpha$IFN is INF$\alpha$-2b, a recombinantly-made product of the Schering Corp., Kenilworth, N.J. Alternate embodiments, where the foreign $\alpha$INF is not completely autologous, may be used since the polymeric modification sufficiently reduces antigenic responses.

A key, however, is that the non-autologous $\alpha$IFN has sufficient bioactivity or $\alpha$IFN effect such as antiviral activity in the target mammal. Other substances including $\alpha$IFN fractions or predecessor polypeptides can also be included in the conjugates of the present invention. As used herein, "α-IFN effect in mammals" means any substance which demonstrates in vivo activity corresponding to that observed with αIFN's. These substances are prepared by using techniques known to those of ordinary skill in the art such as tissue culture, extraction from animal sources or by recombinant DNA methodologies. Transgenic sources of αIFN and related moieties are also contemplated. Such materials are obtained from transgenic animals, i.e. mice, pigs, cows, etc. where the αIFN protein is expressed in milk, blood, or tissues. It is also understood that the recombinant techniques could also include a glycosylation site for addition of a carbohydrate moiety on the recombinantly-derived polypeptide. The method by which the αIFN is prepared for the conjugates of the present invention is not limited to those described herein.

αIFN has certain advantages over other interferon species such as β and γ IFNs. For purposes of the present invention, the αIFN's are preferred because of their biochemical and serological properties. In particular, αIFN has documented antiviral properties and diffuses more effectively into the bloodstream than other interferons. An important aspect of the present invention is the recognition that unlike other IFN's, αIFN has three lysines in active site area of the polypeptide. It has been surprisingly determined that the attachment techniques described herein sufficiently protect these lysines from polymeric attachment (and inactivation) during conjugation. As will be discussed below, most polymers attach at αIFN lysines which are not associated with bioactivity.

2. Non-Antigenic Polymers

To conjugate the αIFN to polymers such as poly(alkylene oxides), one of the polymer hydroxyl end-groups is converted into a reactive functional group which allows conjugation. This process is frequently referred to as "activation" and the product is called an "activated poly(alkylene oxide)". Other substantially non-antigenic polymers are similarly "activated" or functionalized.

The activated polymers are reacted with αIFN so that attachment preferably occurs at ε-amino groups of lysines. Free carboxylic acid groups, suitably activated carbonyl groups, oxidized carbohydrate moieties and mercapto groups if available on the IFN can also be used as attachment sites.

In a preferred aspect of the invention, urethane linkages are formed between with the αIFN ε amino groups and the activated polyalkylene oxides. Preferably, the urethane linkage is formed as described in commonly owned U.S. Pat. No. 5,122,614, the disclosure of which is hereby incorporated by reference. This patent discloses the formation of N-succinimide carbonate derivatives of polyalkylene oxides. Polymers activated with amide-forming linkers or the like are also contemplated. Other functional groups which facilitate attachment of the polymer to the IFN via ε amino or other groups are also contemplated.

Among the substantially non-antigenic polymers, monoactivated, alkyl-terminated polyalkylene oxides (PAO's), such as monomethyl-terminated polyethylene glycols (mPEG's) are preferred; bis-activated polyethylene oxides are also contemplated for purposes of cross-linking αIFN's or providing a means for attaching other moieties such as targeting agents for localizing the polymer-αIFN conjugate in a particular area such as, for example, the liver.

Suitable polymers will vary substantially by weight. Polymers having molecular weights ranging from about 200 to about 35,000 are usually selected for the purposes of the present invention. Molecular weights of from about 1,000 to about 15,500 are preferred and 2000 to about 12,500 are particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained. In addition to mPEG, $C_{1-4}$ alkyl-terminated polymers are also useful.

As an alternative to PAO-based polymers, effectively non-antigenic materials such as dextran, polyvinyl pyrrolidones, polyacrylamides, polyvinyl alcohols, carbohydrate-based polymers and the like can be used. Those of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

3. Surfactants

In one preferred aspect, the surfactants used in the processes of the present invention are ionic-type agents. One particularly preferred agent is sodium dodecyl sulfate, (SDS). Other ionic surfactants such as lithium dodecyl sulfate, quaternary ammonium compounds, taurocholic acid, caprylic acid, decane sulfonic acid, etc can also be used. Non-ionic surfactants can also be used. For example, materials such as polyoxyethylene sorbitans (Tweens), polyoxyethylene ethers (Tritons) can be used. See also Neugebauer, *A Guide to the Properties and Uses of Detergents in Biology and Biochemistry* (1992) Calbiochem Corp. The only limitations on the type of surfactant used in the processes of the invention are that they do not cause substantial denaturation of the IFN and do not completely inhibit polymer conjugation. The surfactants are present in the reaction mixtures in amounts from about 0.01–0.5%; preferably from 0.05–0.5%; and most preferably from about 0.075–0.25%. Mixtures of the surfactants are also contemplated.

While applicants are not bound by theory, the surfactants are thought to provide a temporary, reversible protecting system during the polymer conjugation process. αIFN contains three lysines in the active site region. This relatively positive-charged area of the polypeptide has been found to undergo substantial polymer conjugation during solution-based processes without some kind of protection. This results in substantial or complete loss of bioactivity. The surfactants have been found to be surprisingly effective in selectively discouraging polymer conjugation in this area while allowing lysine-based conjugation to proceed on other areas of the polypeptide.

4. Reaction Conditions

Conjugation reactions, sometimes referred to as PEGylation reactions, are often carried out in solution without regard to where the polymer will attach to the protein. Such techniques however have proven to be inadequate for conjugating αIFN. As described above, it has been determined that a key to maintaining bioactivity is to substantially avoid including those lysines in the active site in the polymer coupling process.

The processes of the present invention achieves this goal by carrying out the conjugation reaction in the presence of a surfactant with relatively small molar excesses of the polymer with respect to the αIFN. The process is carried out with about 1–8-fold molar excesses; preferably about 1.5–7-fold molar excesses and most preferably about 1.75–5-fold molar excesses. In an alternative aspect of the invention, conjugation is effected using small molar excesses of activated polymer without a surfactant.

The process preferably includes combining the αIFN in solution with the surfactant prior to introducing the activated polymer. The complete conjugation reaction can be carried out at about room temperature, 20°–25° C. It is also preferred that the coupling reaction be allowed to proceed for rather short periods of time, i.e. 1–2 hours, before quenching.

5. Fractionation of Conjugates

The inventive process produces conjugates having varying degrees of polyalkylene oxide substitution. Residual unconjugated PAO's and αIFN can also be present. This mixture is typically in a reaction buffer containing one or more of phosphate, chloride and bicarbonate anions. The PAO, αIFN and conjugate mixture is preferably fractionated in a buffer solution containing from about 1–10 mg/ml PAO-αIFN conjugates. Suitable solutions have a pH of from about 7.0 to about 9.0 and preferably from about 7.5 to about 8.5. The solutions preferably contain one or more buffer salts selected from KCl, NaCl, $K_2HPO_4$, $KH_2PO_4$, $Na_2HPO_4$, $NaH_2PO_4$, $NaHCO_3$, $NaBO_4$, $(NH_4)_2CO_3$ and glycine NaOH. Sodium phosphate buffers are preferred.

Depending upon the reaction buffer, the PAO-αIFN conjugate solution may first have to undergo buffer exchange/ultrafiltration. For example, the PAO-αIFN conjugate solution can be ultrafiltered across a low molecular weight cut-off (10,000 to 30,000 dalton) membrane which will also remove most surfactants as well.

The fractionation of the conjugates into desired species is preferably carried out using an anion exchange medium. Such media are capable of selectively binding those PAO-αIFN conjugates having 1–4 PAO strands, excess PAO and unmodified αIFN. This fractionation occurs since the αIFN molecules of various degrees of substitution will have isoelectric points which vary in a somewhat predictable fashion. For example, the isoelectric point of αIFN is determined by the number of available lysine residues available on the surface of the protein. These lysine residues also serve as the point of attachment of polyalkylene oxide conjugates. Therefore, as the degree of substitution of polyalkylene oxide increases, the isoelectric point decreases, and the ability of the conjugate to bind to an anion exchange resin weakens.

The use of strongly polar anion exchange resins are especially preferred for the method of the present invention. For this reason, quaternary amine coated anion exchange resins are utilized. The quaternary amine resin may be coated onto either a polymeric or silica matrix; however, polymeric matrices are preferred. A number of tetramethylamine, or quaternary methylamine, anion exchange resins are commercially available, coated onto the support matrices. Included among the commercially available quaternary anion exchange resins suitable for use with the present invention are Q-HD, QA TRISACRYL® and QMA-SPHEROSIL®, quaternary amine resins coated onto a polymer matrix, manufactured by IBF of Garenne, France, for Sepracor of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Millford, Mass. and PEI resins manufactured by JT Baker of Phillipsburg, N.J., may also be used.

The anion exchange resin is packed in the column and equilibrated by conventional means. A buffer having the same pH and osmolality as the conjugated αIFN solution is used. The conjugate-containing solution is then adsorbed onto the column. At the completion of the loading, a gradient flow of an elution buffer with increasing salt concentrations is applied to the column to elute the desired fractions of polyalkylene oxide-conjugated αIFN. The fractions are of essentially uniform molecular weight and degree of substitution.

Preferred polyalkylene oxide conjugate fractions have 1–4 polyalkylene oxide strands per αIFN molecule. Preferably the fraction contains about 1–3 and most preferably about 2 PAO strands per αIFN molecule. The elution buffer preferably contains one or more salts selected from KCl, NaCl, $K_2HPO_4$, $KH_2PO_4$, $Na_2HPO_4$, $NaH_2PO_4$, $NaHCO_3$, $NaBO_4$ and $(NH_4)_2CO_3$. These fractions are substantially free of other conjugates. Any unconjugated species can then be backwashed from the column by conventional techniques.

Techniques utilizing multiple isocratic steps of increasing concentration can also be used. Multiple isocratic elution steps of increasing concentration will result in the sequential elution of PAO-αIFN conjugates. The degree of polyalkylene oxide-conjugation within each fraction will be substantially uniform. However, the degree of polyalkylene oxide conjugation for each fraction will decrease with elution time. Ion exchange purification of PAO-αIFN conjugates can also be carried out with, for example, a Q-HD Column from Sepracor along with a dilute sodium phosphate solution (10 mM $NaPO_4$ ion). The sample is washed with 10 mM $NaPO_4$ to remove any unreacted PAO and thereafter a step gradient elution with NaCl is used. Elution with 10 mM NaCl recovers fractions containing conjugates with greater than 3 polymer strands PAO per IFN; elution with 50 mM NaCl recovers conjugates containing 1–2 strands; elution with 150 mM NaCl recovers unmodified IFN.

The temperature range for elution is between about 4° C. and about 25° C. Preferably, elution is carried out at a temperature of from about 6° C. to about 22° C. The elution of the PAO-αIFN fraction is detected by UV absorbance at 254 nm. Fraction collection may be achieved through simple time elution profiles. The preferred fractions can also be pooled in the elution buffer.

6. Methods of Treatment

Another aspect of the present invention provides methods of treatment for various medical conditions in mammals. The methods include administering an effective amount of αIFN-polymer conjugate which has been prepared as described herein to a mammal in need of such treatment. The conjugates are useful for, among other things, treating interferon-susceptible conditions or conditions which would respond positively or favorably as these terms are known in the medical arts to interferon-based therapy. Thus, without limitation, the interferon conjugates can be used to treat conditions which would benefit from the inhibiting replication of interferon-sensitive viruses. In addition, the conjugates can be used to modify various immune responses including inhibition of antibody response to antigenic challenge, inhibition of hypersensitivity reactions, regulation of NK cell activity enhancement of cytotoxic T cell activity, modulate prostaglandin production and enhance phagocytosis by macrophages.

Additional conditions in which the IFN-polymer conjugates can be used include hairy cell leukemia, venereal or genital warts (condylomata acuminata), AIDS-Related Kaposi's sarcoma, hepatitis and hepatitis-like viral conditions including hepatitis-B and chronic hepatitis non-A, non-B/C.

The amount of the α-IFN polymer conjugate administered to treat the conditions described above is based on the IFN activity of the polymeric conjugate. It is an amount that is sufficient to significantly affect a positive clinical response. The maximal dose for mammals including humans is the highest dose that does not cause clinically-important side effects. For purposes of the present invention, such clinically important side effects are those which would require cessation of therapy due to severe flu-like symptoms, central nervous system depression, severe gastrointestinal disorders, alopecia, severe pruritus or rash. Substantial white and/or red blood cell and/or liver enzyme abnormalities or anemia-like conditions are also dose limiting.

Naturally, the dosages of the various αIFN compositions will vary somewhat depending upon the αIFN moiety and polymer selected. In general, however, the conjugate is administered in amounts ranging from about 100,000 to about several million $IU/m^2$ per day, based on the mammal's condition. The range set forth above is illustrative and those skilled in the art will determine the optimal dosing of the conjugate selected based on clinical experience and the treatment indication.

The αIFN-polymer conjugates of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions will be chiefly by the parenteral route although oral or inhalation routes may also be used depending upon the needs of the artisan.

EXAMPLES

The following examples serve to provide further appreciation of the invention but are not meant in any way to restrict the effective scope of the invention.

Example 1

Preparation of rαIFN-$PEG_{5000}$ in presence of SDS (0.1%)

In this example, recombinant αIFN-2b, (rαIFN), a product of the Schering Corporation, Kenilworth, N.J. was conjugated with activated polyethylene glycol-N-succinimide carbonate (SC-PEG) as described in U.S. Pat. No. 5,122,614. The polymer had a molecular weight of about 5000.

36 mg of the rαIFN was dialyzed into 0.1 molar sodium phosphate pH 7.5 using a Centricon-10 (a product of the Amicon Corporation of Beverly, Mass.). The final concentration of rαIFN was about 3 mg/ml. 0.1 ml of 10% SDS was added to the rαIFN and was allowed to incubate at room temperature for 10 minutes. Thereafter, 42 mg of SC-$PEG_{5000}$ was added to the protein-SDS solution and stirred at room temperature for two hours and then quenched with glycine. Next, the reaction mixture was dialyzed into 10 mM sodium phosphate pH 8 to fractionate the PEGylated IFN using a Centricon-30.

Example 2

Preparation of rαIFN-$PEG_{12000}$ in presence of SDS (0.1%)

In this Example, the steps of Example 1 were repeated except that the polyethylene glycol had a molecular weight of about 12000. Reaction steps were exactly the same to provide the $PEG_{12000}$ conjugate.

Example 3

Fractionation of 2$PEG_{5000}$rαIFN

In this Example the conjugates prepared in accordance with Example 1 were fractionated to obtain the desired 2-$PEG_{5000}$ fraction. The PEG-αIFN in sodium phosphate buffer was loaded onto a QHD anion exchange column. The 2-PEG fraction was eluted with a gradient from 0 to 400 mm sodium chloride in 10 Mm phosphate pH 8. The 2-PEG fraction was verified with using size exclusion chromatography and SDS-Page.

Example 4

Fractionation of 2$PEG_{12000}$rαIFN

The polymer conjugates of Example 2 were fractionated in the manner described in Example 3 and verified in the same manner.

Examples 5–8

In these examples, additional preparations of $PEG_{12000}$-rαIFN were prepared as described previously except that no surfactant was used. The samples were tested for retained activity and PEG number. The results are provided below in the table.

TABLE 1

| PREPARATION | ACTIVITY (CPE) % OF CONTROL | PEG # |
|---|---|---|
| Example 6 | 26 | 1.2 |
| Example 7 | 26 | 1.3 |
| Example 8 | 24 | 1.0 |

Example 9

Comparative Data

In this example, the product of Example 3, (SDS-2-PEG-$_{5000}$rαIFN), 2-$PEG_{5000}$rαIFN made in the absence of a surfactant and unconjugated rαIFN were tested. Activity was determined using a CPE assay with EMC virus challenging A549 human lung carcinoma cells. Circulating life was determined using an average value obtained from the blood of 3 rats in a group receiving 1 million units, with time points taken over 7 days.

TABLE 2

| | ACTIVITY (%) | VIRAL PROTECTION ASSAY $IC_{50}$ (pg/ml) | CIRCULATING HALF LIFE α PHASE (HRS.) |
|---|---|---|---|
| A. IFN-SDS 2-$PEG_{5000}$ | 69 | 2.2 | 5.8 |
| B. IFN-$PEG_{5000}$ | 30 | 4.0 | 6.8 |
| C. IFN | 100 | 1.5 | 0.17 |

This data clearly shows the advantages of the inventive process. Retained activity is over twice as great as that obtained using standard techniques.

Example 10

In this example, various pharmacokinetic data was generated using the various 2PEG-rαIFN conjugates shown below prepared according to the methods described above. These samples were compared to unmodified IFN according to the protocol set out in Table 3. Sample B was prepared with SDS.

TABLE 3

Retained Activity

| SAMPLE | PEG MOLECULAR WEIGHT | CPE ACTIVITY (% CONTROL) |
|---|---|---|
| A | 5,000 | 35 |
| B | 5,000 | 69 |
| C | 12,000 | 26 |
| D | 12,000 | 26 |

For example:

Table 4

Pharmacokinetic Protocol

ANIMALS: Sprague Dawley (3 rates/time point)

DOSE: $10 \times 10^6$ UN IFN/rat

ROUTE: Subcutaneous (S.C.)

DRUG: 2-PEG-IFNα's 5,000 and 12,000 mol. wt. PEG

TIME POINTS: 0 min., 5 min., 15 min., 30 min., 1 hr., 2 hr., 4 hr., 8 hr., 24 hr., 48 hr., 5 days, and 7 days following drug administration.

ASSAY: CPE Assay using serum samples in an EMC virus and A549 human lung carcinoma.

AUC=Area Under Curve, $C_{max}$, $T_{1/2}\alpha$, $T_{1/2}\beta$—all have their generally ascribed meanings known to those of ordinary skill.

Tables 5 and 6

Summary of Pharmacokinetics Data for PEG-Interferons

TABLE 5

| SAMPLE | $IC_{50}$ (pg/ml) | % ACTIVITY | AUC | Cmax (IU/ml) |
|---|---|---|---|---|
| NATIVE IFNα | 1.52 pg/ml (N = 6) | 100% | 145,720 | 60,000 |
| A | 4.0 pg/ml (N = 3) | 35% | 348,920 | 24,433 |
| B | 2.2 ± 0.5 pg/ml (N = 3) | 69% | 351,037 | — |
| C | 5.8 ± 2.2 pg/ml (N = 3) | 26% | 1,574,682 | 62,750 |

TABLE 6

| SAMPLE | $T_{max}$ (HR) | $T_{1/2}$ α PHASE (HR) | $T_{1/2}$ β PHASE (HR) |
|---|---|---|---|
| NATIVE IFNα | 1 | 0.17 | — |
| A | 4 | 6.8 | 48 |
| B | 2–3 | 5.8 | — |
| C | 8 | 12.1 | 33 |

The foregoing data provide the following conclusions:

2-PEG-rαIFN conjugates prepared with both 5,000 and 12,000 molecular weight have distinct advantages over unmodified interferon in mammals. In the case of subcutaneously administered compositions, $T_{max}$ is substantially increased by the conjugation of the protein with about 2 PEG's. For chronic conditions, longer $T_{max}$'s are desirable and allow clinicians to space out recurring administrations due to the lengthening of the duration of effect. Even more unexpected, however, was the fact that 2-PEG$_{12000}$ conjugates are able to unexpectedly increase AUC by over 10-fold. This effect achieved by the additional polymer weight was not proportional to the dramatic increase in area under the curve. Clearly, therapeutic advantages are realized by this unexpected increase.

What is claimed is:

1. A process for preparing a long-acting alpha-interferon-containing composition, comprising contacting an alpha interferon with from about a 1 to about an 8-fold molar excess of an activated polyalkylene oxide containing an alkyl terminal in the presence of a surfactant under conditions sufficient to form conjugates of said alpha interferon and said polyalkylene oxide having an alkyl terminal and thereafter fractionating the conjugates to isolate the conjugates containing about 1–4 polyalkylene oxide strands per alpha-interferon molecule.

2. The process of claim 1, wherein said molar excess is from about 1.5 to about 7-fold.

3. The process of claim 2, wherein said molar excess is from about 1.75 to about 5-fold.

4. The process of claim 1, wherein polyalkylene oxide containing said alkyl terminal is a polyethylene glycol.

5. The process of claim 1, wherein said polyalkylene oxide is a monomethyl-terminated polyethylene glycol, (mPEG).

6. The process of claim 5, wherein said mPEG is activated with succinimidyl carbonate.

7. The process of claim 5, wherein said mPEG is activated with succinimidyl succinate.

8. The process of claim 5, wherein said mPEG is activated with a hydrazine moiety.

9. The process of claim 1, wherein said polyalkylene oxide polymer has a molecular weight of from about 200 to about 35,000.

10. The process of claim 9, wherein said polyalkylene oxide polymer has a molecular weight of from about 1,000 to about 15,000.

11. The process of claim 10, wherein said polyalkylene oxide polymer has a molecular weight of from about 2,000 to about 12,500.

12. The process of claim 1, wherein said surfactant is ionic.

13. The process of claim 12, wherein said surfactant comprises sodium dodecyl sulfate (SDS).

14. The process of claim 12, wherein said surfactant is selected from the group consisting of lithium dodecyl sulfate, quaternary ammonium compounds, taurocholic acid, caprylic acid, decane sulfonic acid and mixtures thereof.

15. The process of claim 12, wherein said surfactant is present in an amount from about 0.01–0.5%.

16. The process of claim 15, wherein said surfactant is present in an amount of from about 0.05 to about 0.5%.

17. The process of claim 16, wherein said surfactant is present in an amount of from about 0.075 to about 0.25%.

18. The process of claim 1, wherein said surfactant is selected from the group consisting of polyoxyethylene sorbitans, polyoxyethylene ethers and mixtures thereof.

19. The process of claim 1, further comprising isolating the conjugated-alpha interferon species containing from about one to about four polyalkylene oxide strands.

20. The process of claim 19, further comprising separating the conjugated-alpha interferon species containing from about one to about three polyalkylene oxide strands.

21. The process of claim 20, further comprising separating the conjugated-alpha interferon species containing about two polyalkylene oxide strands.

22. The process of claim 1, wherein said alpha interferon is isolated from a mammalian source.

23. The process of claim 22, wherein said alpha interferon is human alpha interferon.

24. The process of claim 22, wherein said alpha interferon is ruminant alpha interferon.

25. The process of claim 24, wherein said ruminant alpha interferon is bovine alpha interferon.

26. The process of claim 22, wherein said alpha interferon is porcine alpha interferon.

27. The process of claim 1, wherein said conjugates isolated after said fractionating step contain about 1–2 polyalkylene oxide strands per alfa interferon molecule.

28. The process of claim 1, wherein said alpha-interferon is interferon alpha 2b.

* * * * *